(12) United States Patent
Krawiec et al.

(10) Patent No.: US 12,370,064 B2
(45) Date of Patent: Jul. 29, 2025

(54) SMART SURGICAL INSTRUMENT PATCH, INSTRUMENTS, AND METHODS OF APPLICATION

(71) Applicant: GLOBUS MEDICAL, INC., Audubon, PA (US)

(72) Inventors: Catherine Krawiec, Conshohocken, PA (US); Mary Siepierski, Bradford, PA (US); Jared Carboy, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 306 days.

(21) Appl. No.: 18/158,161

(22) Filed: Jan. 23, 2023

(65) Prior Publication Data

US 2024/0245531 A1 Jul. 25, 2024

(51) Int. Cl.
*A61F 2/46* (2006.01)
*A61F 2/44* (2006.01)
*A61B 17/00* (2006.01)
*A61B 90/00* (2016.01)
*A61F 2/30* (2006.01)

(52) U.S. Cl.
CPC .......... *A61F 2/4657* (2013.01); *A61F 2/4455* (2013.01); *A61F 2/4611* (2013.01); *A61B 2017/00057* (2013.01); *A61B 2090/0807* (2016.02); *A61F 2002/30579* (2013.01); *A61F 2002/3067* (2013.01); *A61F 2002/4627* (2013.01)

(58) Field of Classification Search
CPC .... A61F 2/4657; A61F 2/4455; A61F 2/4611; A61F 2002/30579; A61F 2002/3067; A61F 2002/4627; A61B 2017/00057; A61B 2090/0807
USPC ................... 606/102, 279; 623/17.11–17.16
See application file for complete search history.

(56) References Cited

U.S. PATENT DOCUMENTS

2003/0149349 A1\* 8/2003 Jensen ................ A61B 5/6833
600/587

\* cited by examiner

*Primary Examiner* — Jessica Weiss (57) ABSTRACT

Smart surgical instrument patches, instruments, systems, and methods. The smart surgical instrument patch may include a flexible substrate with electronic components electronically connected to one another. The electronic components may include one or more sensors, a processor, a power source, and a wireless communication unit. The patch may be affixed to an instrument, such as an inserter for installing an expandable implant. During operation of the instrument, the smart surgical instrument patch may provide real time information to the user, such as amount of implant expansion and lordosis profile.

10 Claims, 9 Drawing Sheets

SMART SURGICAL INSTRUMENT PATCH, INSTRUMENTS, AND METHODS OF APPLICATION

FIELD OF THE INVENTION

The present disclosure relates to instruments for installing surgical devices, such as expandable fusion devices, and smart surgical patches attachable to such instruments for electronically indicating parameters, such as implant expansion and/or lordotic profile.

BACKGROUND

During transforaminal and posterior lumbar interbody fusion procedures, for example, an interbody device may be inserted into the intervertebral disc space between adjacent vertebral bodies. The interbody device may provide indirect decompression to nervous tissue and provide a mechanical foundation for subsequent bone fusion through the disc space. Interbody cages may be static in height or may be inserted at a shortened height and expanded to achieve an increased height in-situ. Due to a narrow surgical working channel, height expansion cannot be directly visualized by the surgeon. As such, the user may rely on intra-operative fluoroscopic images or indicator mechanisms on the implant inserter to know the current expanded height of the expandable implant. Referencing fluoroscopic images only yields approximate and relative height measurements, and mechanism-based indicators can cause instruments to be more complex, expensive, and/or more difficult to sterilize.

Similarly, in robotic and navigated workflows associated with expandable interbody spacers, there is no way to know the height of the interbody as it is expanded. The presence of a robot and/or navigation camera stand may make the space cramped and inconvenient to bring C-arms or other imaging systems into the surgical space, and fluoroscopic imaging only provides an approximate profile measurement. As such, there exists a need for an instrument that electronically indicates the amount of implant expansion in situ or other parameters during the procedure.

SUMMARY

To meet this and other needs, and in view of its purposes, the present application provides electronic sensor patches, instruments for installing expandable implants, systems for communication of implant information to a user, and methods for electronically indicating implant expansion, lordotic profile, or other parameters. The smart sensor patch may include a substrate with a plurality of electronic sensors, a power source, and a wireless communicator. The sensor patch may be affixed to an instrument, such as an implant inserter, to obtain and send information about the implant, such as expansion height and lordotic angle. One or more of these features may help to provide more accurate information about the implant in situ, reduce the size, mechanical complexity, and cost of the instrument, and/or make the instrument easier to disassemble, clean, and sterilize.

According to one embodiment, a system for obtaining implant information in real time may include a smart electronic patch, an expandable implant, and an instrument for installing the expandable implant. The smart electronic patch may have a substrate with a plurality of electronic components electronically connected to one another. The plurality of electronic components may include a sensor, a processor, a power source, and a wireless transmitter. The expandable implant may be configured to expand in height and/or lordosis. The instrument may have one or more drivers for expanding the implant. As the driver rotates, the sensor on the patch detects movement to obtain raw sensor data, the processor on the patch translates the raw sensor data to implant information, and the wireless transmitter on the patch sends the implant information to a user display.

The system may include one or more of the following features. The sensors may include a plurality of infrared optic sensors. The instrument may include a rod having a distal tip configured to couple to the expandable implant, a proximal tube with a plurality of indicators readable by the sensor, and a handle for turning the one or more drivers. The handle may include an arm with one or more through openings configured to receive the sensor on the patch. The plurality of indicators may include regularly spaced etched lines placed in a radial pattern around the proximal tube. The smart electronic patch may be pre-sterilized and/or pre-charged. The system may further include an external user display configured to receive the implant information from the wireless transmitter and display the information on a screen for a user.

According to another embodiment, a system for obtaining surgical information in real time my include an inserter instrument and a smart electronic patch. The inserter instrument may extend along a central longitudinal axis and may include an outer tube having a distal tip configured to attach to an implant, a pair of drivers positioned through the outer tube for expanding the implant, a clutch collar moveable to control rotation of the drivers, and a handle for turning one or both of the drivers. The smart electronic patch may be affixed to the handle of the inserter instrument. The patch may have a pair of sensors for viewing a plurality of indicators on the outer tube of the instrument, and a third sensor for viewing an indicator on the clutch collar of the instrument. The third sensor may be configured to detect a position of the clutch collar. As the handle rotates, the pair of sensors on the patch may be configured to detect the plurality of indicators on the outer tube.

The system may include one or more of the following features. The clutch collar may include a proximal hub with a plurality of splines and a distal hub with a plurality of splines separated by a flange. The clutch collar may be configured to translate along the central longitudinal axis. The outer tube may define a seat for receiving the distal hub in a forward position and the handle may define a seat for receiving the proximal hub in a rear position. The indicator on the clutch collar may be an etched line around a perimeter of the flange. The plurality of indicators on the outer tube may include regularly spaced alternating etched lines placed in a radial pattern. The pair of sensors may include infrared sensors having an emitter and a receiver that senses reflected infrared light to obtain a signal. As the pair of sensors pass over the alternating etched lines, the signal alternates between high and low, thereby indicating a change in angular position. The pair of sensors may be spaced n*1.5 cycles away from one another to interpret direction of movement of the handle.

According to another embodiment, a smart electronic patch includes a flexible substrate and a plurality of electronic components. The flexible substrate may have a top surface and a lower surface with an adhesive. The plurality of electronic components may be affixed to the substrate and electronically connected with one another. The plurality of electronic components may include a plurality of sensors, a processor, a power source, a power regulator, and a wireless communication unit. The plurality of sensors may protrude below the lower surface of the substrate and the processor, power source, power regulator, and wireless communication unit may be positioned on the top surface of the substrate.

The patch may include one or more of the following features. The plurality of sensors may include infrared optic sensors. The flexible substrate may include a plurality of laminated layers. The flexible substrate may be a flexible multi-layer printed circuit board. The power source may be a pre-charged battery. The smart electronic patch may be pre-sterilized, for example, prior to shipment.

According to another embodiment, a method of obtaining real time surgical information may include one or more of the following steps in any suitable order: (1) applying a pre-sterilized and pre-charged smart sensor patch to an instrument, the smart sensor patch having a flexible substrate and a plurality of electronic components, such as a plurality of sensors, a processor, a power source, a power regulator, and a wireless communication unit; (2) during use of the instrument, one or more sensors on the patch detect an input from the instrument (e.g., movement of the handle relative to the outer tube) to obtain raw sensor data, the processor on the patch translates the raw sensor data to real time surgical information, and the wireless transmitter on the patch sends the real time surgical information to a user display (e.g., an external user display). The real time surgical information may include various information about the patch, the instrument, the patient, and/or the operation progress or parameters. By way of example, real time information may be obtained on the amount of expansion and/or lordosis of an expandable implant, stiffness of a patient deformity, amount of instrument movement or articulation, internal stress, torque read-out, etc.

According to yet another embodiment, a method of installing an expandable implant may include one or more of the following steps in any suitable order: (1) providing an inserter instrument with an outer tube having a distal tip configured to attach to an implant, a pair of drivers positioned through the outer tube for expanding the implant, a clutch collar moveable to control rotation of the drivers, and a handle for turning one or both of the drivers; (2) affixing a smart sensor patch to the handle, the smart sensor patch having a flexible substrate and a plurality of electronic components, such as a plurality of sensors, a processor, a power source, a power regulator, and a wireless communication unit; (3) temporarily attaching an expandable implant to the distal tip of the outer tube of the inserter instrument for the procedure; (4) preparing an intervertebral disc space, for example, including a discectomy; (5) optionally inserting an endoscopic tube into the disc space; (6) introducing the expandable implant into the disc space in a collapsed configuration and seating it in an appropriate position in the intervertebral disc space; (7) expanding the implant in height and/or lordosis into an expanded position and simultaneously receiving real time information from the smart patch, for example, about the amount of expansion and/or lordosis.

Also provided are kits including smart sensor patches including patch packaging, instruments such as inserter instruments for receiving a sensor patch, expandable implants of various types and sizes, and/or other tools and instruments suitable for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION

Embodiments of the disclosure are generally directed to smart sensor patches, instruments, systems, and methods thereof. Specifically, embodiments are directed to smart sensor patches with one or more sensors configured to provide information, such as implant expansion height and lordotic angle, to the user. The smart sensor patch may be affixed to an inserter assembly configured to install the expandable implant. The sensor patch may be sterile-packed, pre-charged, disposable, and/or wireless. In this manner, the patch does not require a wired connection to transmit data or power, which can cause clutter or hazards in an operating space. Additionally, the patch does not need to be sterilized by the end user or otherwise processed through the sterile processing department (SPD), which makes it more readily available and reduces repeated processing costs.

Sterilizing electronics also has the potential to quickly degrade components and the extreme heat and humidity limits the types of components that can be used. The pre-sterilized and pre-charged patch does not face these issues when the instrument is sterilized and further does not require the end user to buy additional capital equipment to charge, store, and/or sterilize the device. It is also low-profile and is not required to operate the instrument that it is attached to. Thus, if the user does not care to use the patch, they are still able to use the same instrument set without it.

If the patch is used as an alternative to mechanical instrument indication, the system reduces mechanical complexity and cost of the instrument. This can also make the instrument easier to disassemble and clean. The patch is also agnostic to the size of implant, while a mechanical indicator may require a modified design when implants are offered in a variety of heights, lengths, and widths.

Figure 1:
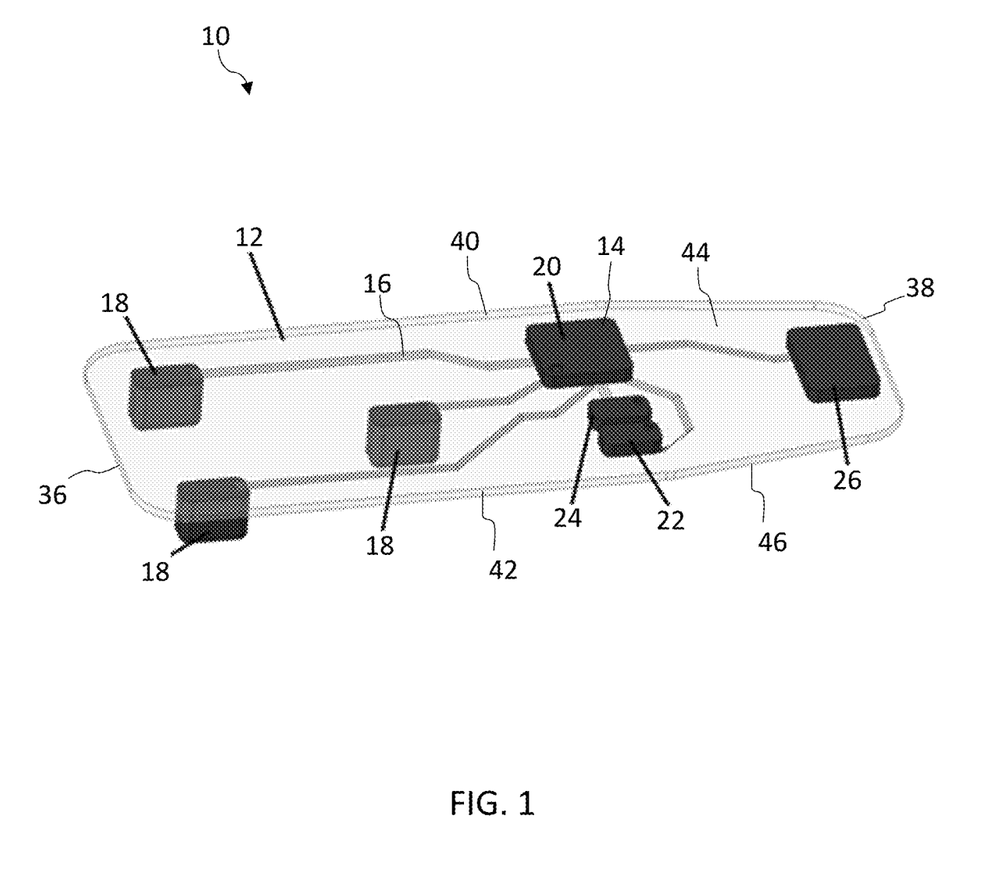
FIG. 1 is a perspective view of a smart sensor patch according to one embodiment.

Referring now to FIG. 1, a smart electronic patch 10 is shown according to one embodiment. The electronic patch 10 includes a substrate 12 supporting a plurality of individual electronic components 14. The electronic components 14 may be electronically connected with one another. For example, the electronic components 14 may be connected by conductive wires or traces 16 or other suitable circuitry. The electronic connection may provide for power flow and/or electronic communication or data transfer between the respective components 14. The electronic components 14 may include one or more of the following or other suitable components: one or more sensors 18, a processor 20, a power source 22, a power regulator 24, and a wireless communication module or unit 26.

The electronic patch 10 may include a plurality of sensors 18. For example, the sensors 18 may include optical sensors, light sensors, color sensors, proximity sensors, touch sensors, infrared sensors, ultrasonic sensors, etc. In one embodiment, the patch 10 may include a collection of optic sensors 18. The optical sensors 18 are capable of detecting light at a specific electromagnetic spectra range, such as visible, infrared, or ultraviolet. The sensors 18 may detect frequency, polarization of light, or wavelength, which change into an electric signal due to the photoelectric effect. In an exemplary embodiment, the patch 10 includes a collection of three infrared optic sensors 18. The infrared optic sensors 18 may have an emitter and a receiver that senses the reflected infrared light. It will be appreciated that any suitable number and type of sensors may be used.

The electronic patch 10 may include an on-board computing unit or processor 20. The computing unit may include a processor or processing unit with memory, storage, and/or software. The processor 20 may be configured to receive and process information from the sensors 18. In particular, the processor 20 may translate raw sensor data, for example, corresponding to implant height and lordotic profile. The processor 20 may then send this information to a user display module 28, for example, via the wireless communication component 26. The user display module 28 may be an external device have its own computing unit or processor. Each of the processors may be configured to accept, process, and/or send information related to the patch 10, instrument 60, implant 200, or other device. The on-board processor component 20 may also be configured to accept user inputs, for example, about the implant type and size, from the display module 28 or other input device.

The electronic patch 10 may include a power source 22 and a power regulator 24. The power source 22 may be an internal battery. The battery 22 may be alkaline, nickel metal hydride, lithium ion, or other suitable battery type. The battery 22 may arrive on the patch 10 fully charged and does not require a wired connection or active charging by the end user prior to use. The power regulator 24 transforms and distributes power from the power source 22 to the different electrical components 14 depending on their needs.

The electronic patch 10 may include a wireless communication module or unit 26, such as a wireless transmitter/receiver. Any information from processor 20 may be sent wirelessly through the wireless communication unit 26 or transmitter. The information, such as implant height and lordotic profile, may be projected on a display 28, such as a monitor or tablet, after the sensor information is processed by the processor 20. In one embodiment, a robotic and/or navigation system may be used to receive and/or send information from the sensor patch 10 and display the information for the user. Further details of robotic and/or navigational systems can be found, for example, in U.S. Pat. Nos. 10,675,094, 9,782,229, and U.S. Patent Publication No. 2017/0239007, which are incorporated herein by reference in their entireties for all purposes.

The electronic components 14 are electrically connected to one another to achieve their desired functions via one or more wires or traces 16 or other suitable circuitry. The electronic connection may provide for power flow and/or electronic communication or data transfer between the respective components based on their needs. Although the patch 20 exemplifies a specific layout with sensors 18, processor 20, power source 22, power regulator 24, and wireless transmitter/receiver 26, it will be appreciated that any suitable type and number of electronic components 14 may be arranged together for the desired functionality of the smart patch 10. For example, in one alternative embodiment, the wireless transmitter/receiver 26 may be removed from the patch and a small user display may be provided directly on the instrument itself.

The electronic patch 10 includes a substrate 12 for supporting the electrical components 14. The electrical components 14 may be positioned on top of, below, within the substrate 12, or at any other suitable location. In one embodiment, the substrate 12 includes a flexible electronic substrate. The flexible substrate 12 may be a thin, heat-resistant material formed of plastic or polymers, such as polyimide or polyethylene terephthalate (PET), metal foil, fiberglass, flex glass, or other suitable materials. The substrate 12 may have an adhesive back configured to adhere the patch 10 to the instrument or other device. In an exemplary embodiment, the substrate 12 is a plastic, adhesive printed circuit board (PCB) substrate.

Figure 2:
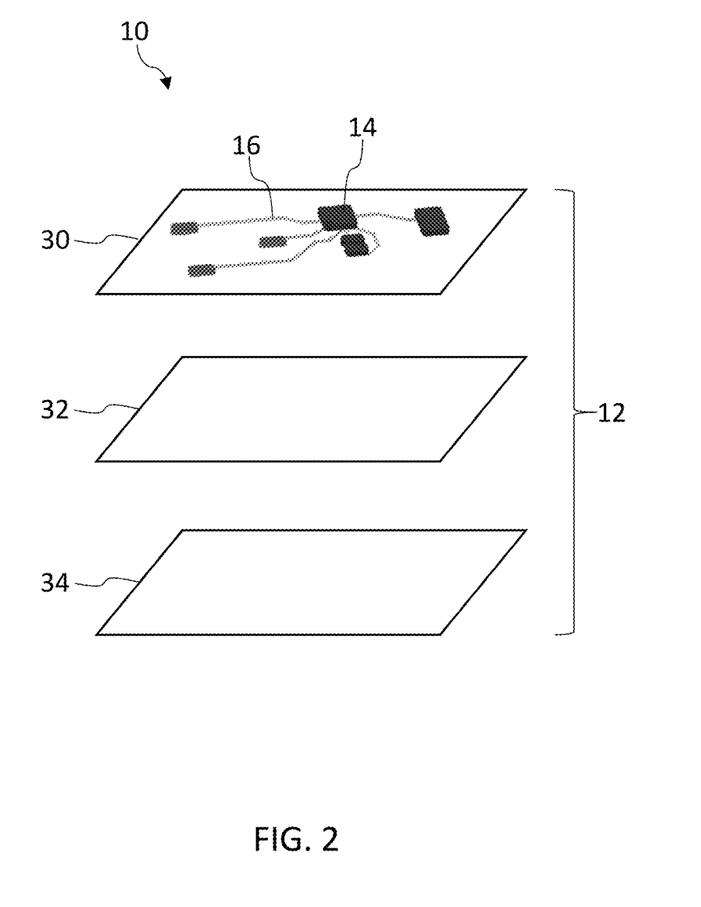
FIG. 2 is an exploded view of a multi-layer smart sensor patch according to one embodiment.

With further emphasis on FIG. 2, the substrate 12 may be composed of multiple layers 30, 32, 34. For example, the substrate 12 may include a top layer 30, one or more mid-layers 32, and a bottom layer 34. Although three layers are shown, it will be appreciated that the substrate 12 may have any suitable number of layers. In the case of a printed circuit board (PCB), the patch 10 may comprise a single layer PCB, a double layer PCB, or a multilayer PCB. The PCB may include one or more fiberglass layers, copper layers, soldermask layers, silkscreen layers, etc. as will be generally appreciated in the art. The layers 30, 32, 34 may be laminated or otherwise joined together. The laminated sandwich structure may include one or more conductive layers, for example, with a pattern of traces 16, and insulating layers to achieve the desired functionality. The bottom layer 34 or an underside thereof may include an adhesive layer, coating, or area configured to secure the patch 10 to a device, such as the inserter instrument 60.

The substrate 12 may be sized and dimensioned in order to attach to a device, such as the inserter instrument 60. For example, the shape of the substrate 12 may be square, rectangular, polygonal, circular, oval, or of any suitable shape to affix to the instrument. As shown in FIG. 1, the patch 10 may have a front end 36, an opposite rear end 38, and two sides 40, 42, connecting the front and rear ends 36, 38. The sides 40, 42 may taper in width toward the rear end 38. The corners may be generally rounded. The patch 10 may include a top side or upper surface 44 and a bottom or lower surface 46. The lower surface 46 may have an adhesive coating or layer configured to secure the patch 10. The electrical components 14 may be positioned on the upper surface 44, the bottom surface 46, or in between the substrate 12.

The electronic components 14 may be arranged around the substrate 12 in a desired configuration. In the embodiment shown in FIG. 1, a pair of sensors 18 spaced in parallel are located near the front end 36 and protrude or project below the lower surface 46 of the patch 10. A third sensor 18 is located more centrally and also protrudes below the lower surface 46. The wireless connector 26 is positioned near the rear end 38 and is located on the upper surface 44 of the patch 10. The processor 20, power source 22, and power regulator 24 are located centrally between the third sensor 18 and the wireless connector 26 and are positioned on the upper surface 44 of the patch 10. Although a specific arrangement and configuration of electronic components 14 are shown, it will be appreciated that the components 14 may be located and interconnected in any suitable manner.

The smart sensor patch 10 may be deliverable in a sterile peel-pack with a full battery charge. The pre-sterilized and pre-charged patch 10 may be shipped flat, for example, or in separate packaging. When ready for use, the pre-sterilized patch 10 may be configured to flex to conform to the instrument when the adhesive side 46 is applied to the instrument surface. Before use, the connection for the power source 22 to the rest of the circuit may be interrupted by a plastic strip. When ready for use, the user removes the plastic interrupter strip after opening the package, which begins the flow of power. The pre-sterilized, pre-charged patch 10 may be configured to last long enough for a single use or case. Following the surgical case, the patch 10 may be thrown away.

Figure 3:
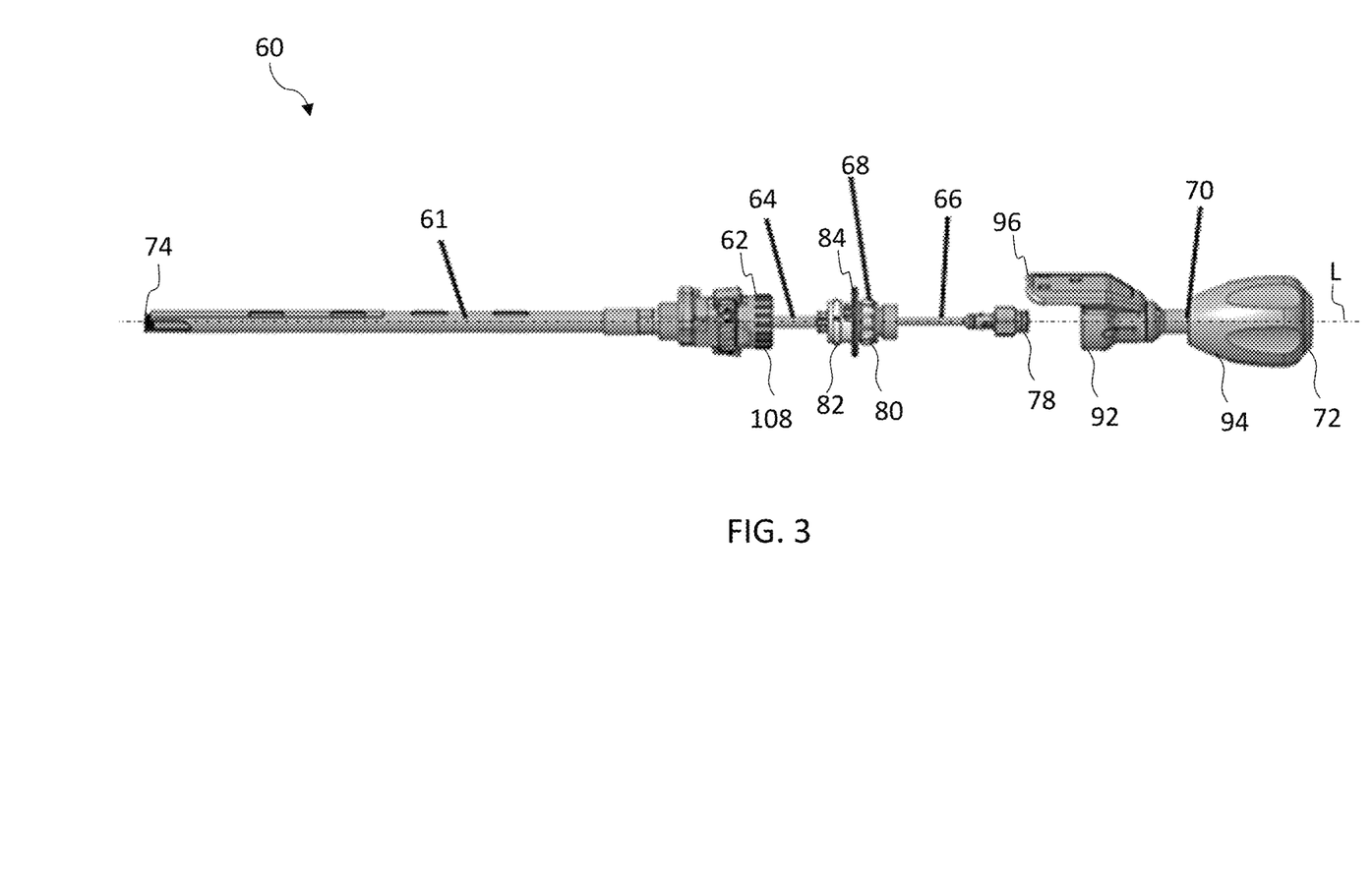
FIG. 3 is an exploded view of an inserter instrument assembly for installing an expandable implant according to one embodiment.
Figure 4A:
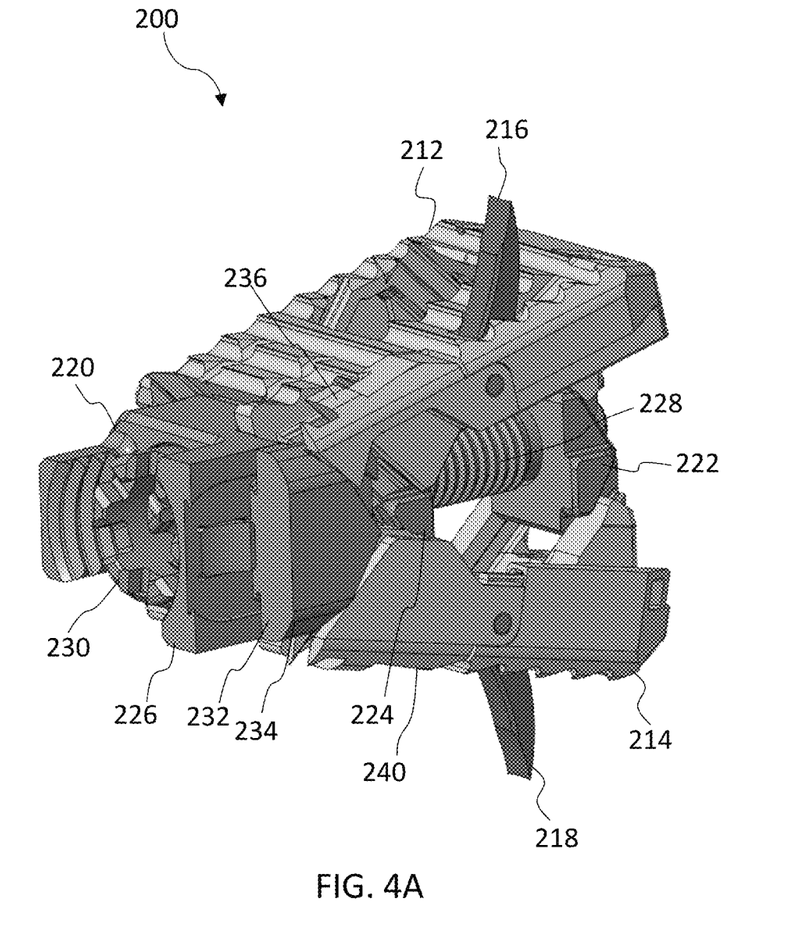
FIGS. 4A-4C show an expandable interbody implant according to one embodiment.
Figure 4B:
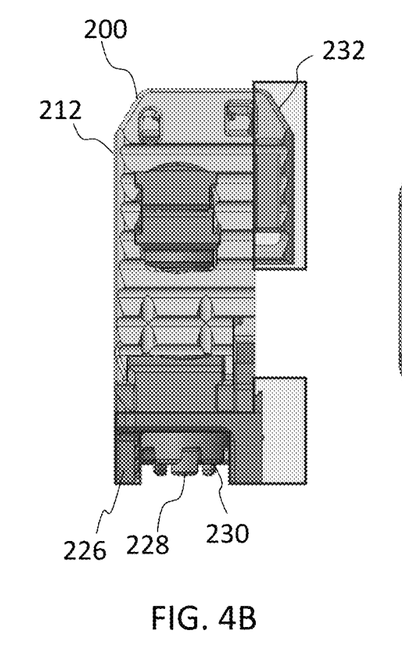
Figure 4C:
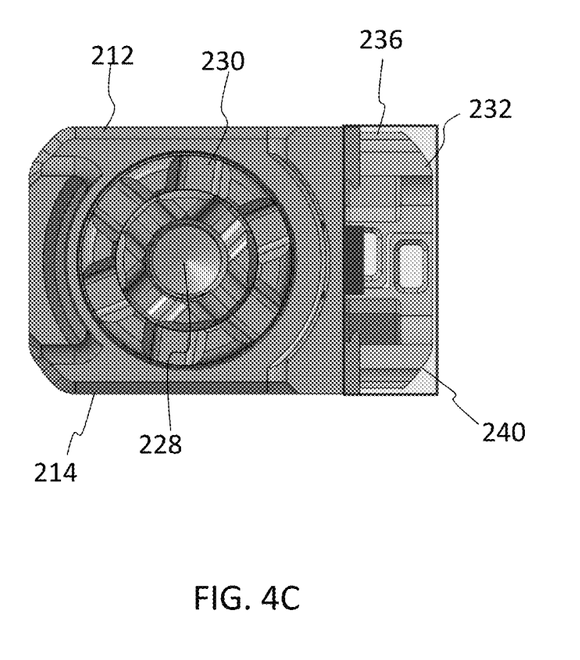

Turning now to FIG. 3, an inserter instrument 60 is shown according to one embodiment. The inserter instrument 60 is configured to install an expandable implant 200, for example, as shown in FIGS. 4A-4C. The inserter 60 includes a threaded rod 61 and rigid tube 62 that hold the implant to the instrument 60, two independent drivers 64, 66 that drive the anterior and posterior height of the implant, a clutch collar 68 that is translated forward and backward to control engagement with either a single driver or both drivers 64, 66, and a driver handle 70 that engages with the back of either one or both drivers 64, 66 depending on the position of the clutch collar 68. The distal engagement of these two drivers 64, 66 with an implant, such as implant 200, as well as implant expansion from the combination of drivers is described in more detail in U.S. patent application Ser. No. 17/540,381, which is incorporated by reference herein in its entirety for all purposes.

As shown in FIGS. 4A-4C, the expandable interbody implant 200 may include an upper endplate 212, a lower endplate 214, an upper deployable spike 216, and a lower deployable spike 218. The upper and lower spikes 216, 218 may be deployed by a sidecar assembly 232, which may include a sidecar carrier 234 configured to move an upper carrier endplate 236 coupled to upper anchor or spike 216 and a lower carrier endplate 240 coupled to lower anchor or spike 218. The main upper and lower endplates 212, 214 and upper and lower carrier endplates 236, 240 are configured to be expanded by an actuator assembly 220, which may include a front ramp 222, a middle ramp 224, and a rear ramp 226 moveable via an actuator or central drive screw 228 and an outer drive screw or nut 230. The anterior and posterior heights of the implant 200 may be independently adjustable for continuous adjustment of height and lordotic profile. More details of implant 200 are described in U.S. patent application Ser. No. 17/540,381, which is incorporated by reference herein in its entirety for all purposes. Although implant 200 is exemplified herein, it will be appreciated that any suitable implant or device may be used in connection with the instruments and electronic patches described herein.

The inserter instrument 60 extends from a proximal end 72 to a distal end 74 along a central longitudinal axis L. The threaded rod 61 and rigid tube 62 may form a hollow outer tube or cannula defining a central channel therethrough. The threaded rod 61 extends from the rigid tube 62 to the distal end 74, thereby forming a distal tip for engagement with the implant 200. The proximal rigid tube 62 may define a recess or seat for receiving a portion of the clutch collar 68 when in the forward position. The first outer driver 64 is positionable through the outer tube 62 and rod 61 such that its tip is configured to engage with and rotate the drive nut 230 on the implant 200. The outer driver 64 is cannulated such that the second inner driver 66 is positionable through the outer driver 64. In this manner, the inner and outer drivers 64, 66 are coaxial about central longitudinal axis L. The tip of the inner driver 66 is configured to engage with and rotate the central drive screw 228 of the implant 200. The proximal end 78 of the inner driver 66 is attachable to the handle 70, for example, via a threaded connection or other suitable interface.

The clutch collar 68 is moveable to control engagement with the drivers 64, 66. In particular, the clutch collar 68 is configured to translate up and down the instrument 60 along the longitudinal axis L to engage with the handle 70 or the outer tube 62, respectively. The clutch collar 68 includes a proximal hub 80 and a distal hub 82 separated by a flange 84. The proximal hub 80 may be in the form of a round gear with a plurality of teeth or splines 86 around the perimeter of the proximal hub 80. The splines 86 may be uniformly distributed around the outer body of the proximal hub 80. Similarly, the distal hub 82 may include a round gear having a plurality of teeth or splines 88 around the perimeter of the distal hub 82. The flange 84 divides the clutch collar 68 and forms a radial ring separating the hubs 80, 82. A marker 90, such as an etched line or ring, may be provided around a lip or periphery of the flange 86. Depending on the position of the clutch collar 68, the proximal hub 80 is receivable in a seat in the handle 70 or the distal hub 82 is receivable in a seat in the proximal end of the outer tube 62.

Figure 5A:
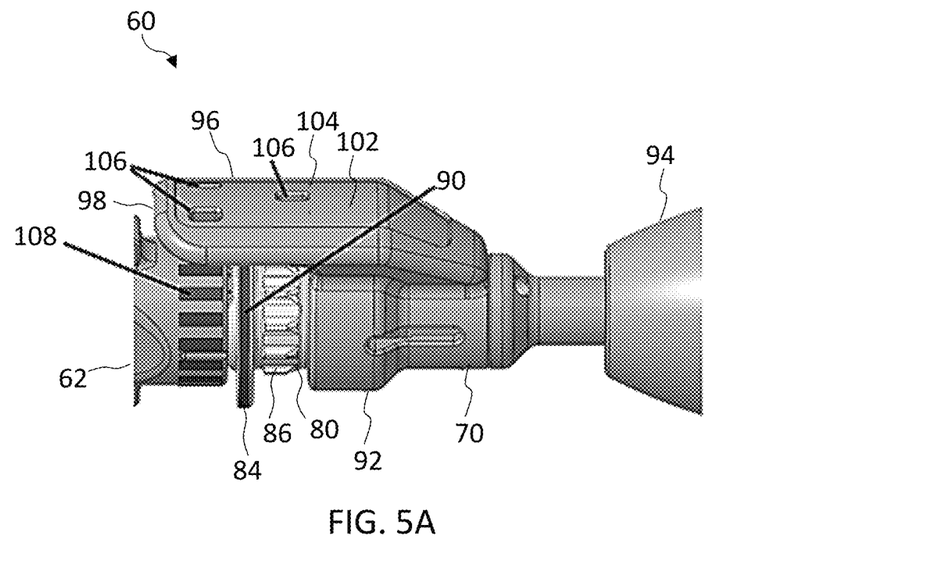
FIGS. 5A-5B show close-up views of the inserter assembly with the clutch in a forward position and in a rear position, respectively.
Figure 5B:
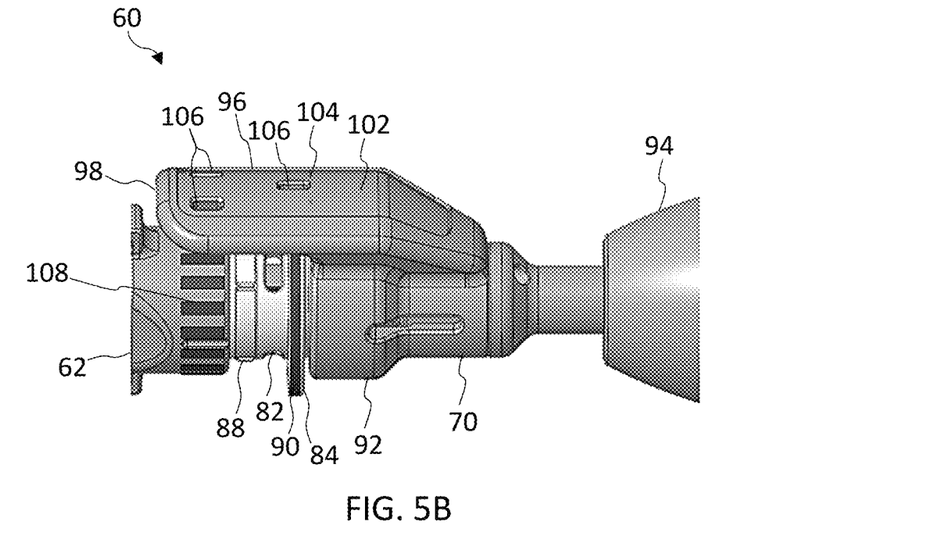

With further emphasis on FIGS. 5A-5B, movement of the clutch collar 68 is shown. The clutch collar 68 may be linearly translated along longitudinal axis L between a front position and a rear position. FIG. 5A shows the clutch 68 in the front or forward position and FIG. 5B shows the clutch 68 in a back or rear position. The inner driver 66 is always engaged with the driver handle 70. The clutch collar 68 is rotationally locked with the outer driver 64. In the rear position as shown in FIG. 5B, the splines 86 on the clutch collar 68 engage with internal splines on the driver handle 70, such that they are rotationally locked. In this way, with the clutch collar 68 in the rear position, both the inner and outer drivers 64, 66 rotate at the same rate. When the clutch collar 68 is in the forward position as shown in FIG. 5A, the splines 88 on the collar 68 engage with internal splines on the rigid tube 62, such that they are rotationally locked, and the splines 86 on the proximal hub 80 that were engaged with the driver handle 70 are unengaged. In this way, when the clutch collar 68 is forward, the driver handle 70 only turns the inner driver 64, and the splines 88 on the rigid tube 62 prevent the outer driver 66 from being turned.

The handle 70 includes a base 92 with a recess or inner seat configured to receive the proximal hub 80 in the rear position (as shown in FIG. 5B). A palm handle 94 connects to the base 92, for example, with a stem. The palm handle 94 may be rotated by a user to apply a torque to the respective driver 64, 66. An arm 96 extends distally and overhangs the base 92 of the handle 70. The arm 96 includes a free distal end 98, an upper face 102, and an opposite lower face. The upper face 102 may defines an optional recess 104 configured to receive the smart patch 10. The recess 104 may be sized and dimensioned to be substantially the same size or slightly larger than the outer dimensions of the patch 10.

Figure 6A:
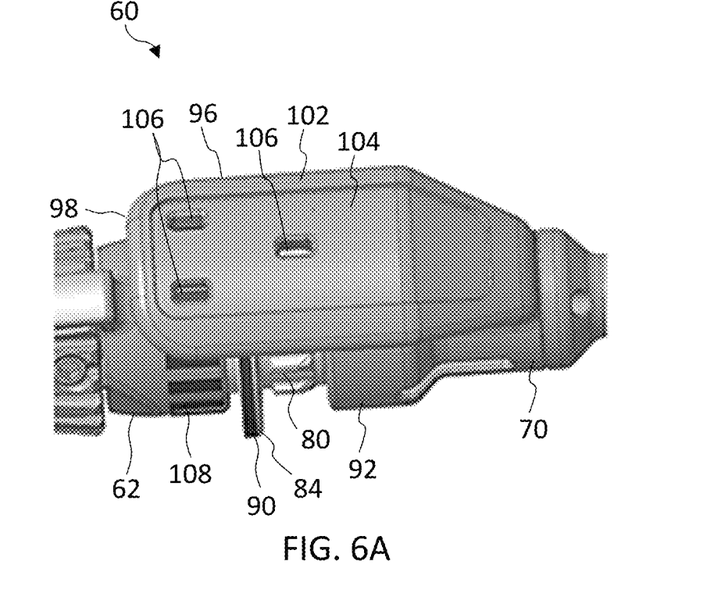
FIGS. 6A-6B show close-up views of the driver handle with sensor-accepting features before the sensor patch is applied and after the sensor patch is applied, respectively.
Figure 6B:
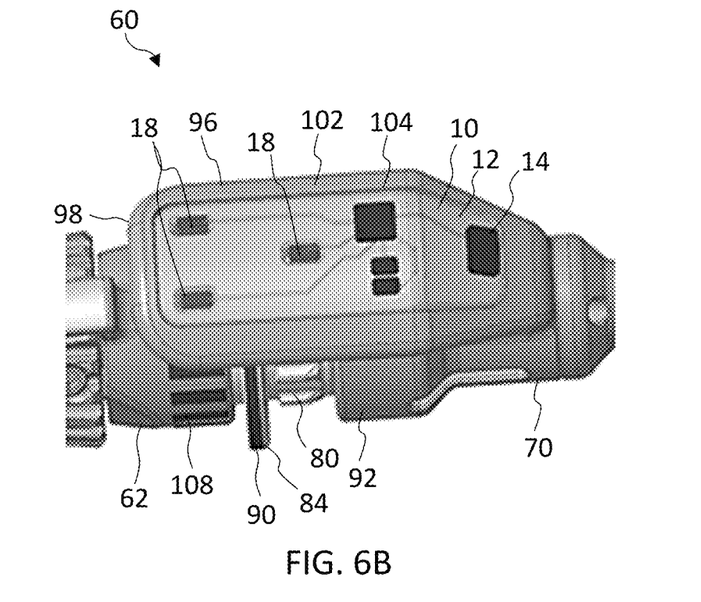

As best seen in FIGS. 6A-6B, the arm 96 of the handle 70 defines one or more through openings 106 configured to align with or receive the sensors 18 from the smart patch 10. FIG. 6A shows the driver handle 70 with the sensor-accepting openings 106 before the patch 10 is applied, and FIG. 6B shows the patch 10 affixed to the arm 96 of the handle 70 with the sensors 18 seated in the openings 106. The openings 106 may extend from the upper face 102 through to the lower face of the arm 96, thereby providing a line of sight to the inner components of the instrument 60 (e.g., the rigid outer tube 62 and moveable clutch collar 68). In particular, a pair of openings 106 may be positioned near the free end 98 of the arm 96 and a third opening 106 may be located centrally and more proximally, which mimics the sensor placement on the patch 10.

The three infrared optic sensors 18 on the patch 10 may be positioned such that they line up with the accepting openings 106 through the arm 96 of the inserter driver handle 70. In particular, the distal pair of openings 106 may be configured to receive patch sensors 18 that view one or more indicators 108 on the proximal end of the outer tube 62. The indicators 108 on the outer tube 62 may include a pattern of dots, lines, or other markings. The pattern may form an alternating and repeating pattern around the outer tube 62. In one embodiment, the outer tube 62 has regularly spaced etched lines 108 placed in a radial pattern. The openings 106 in the arm 96 of the driver handle 70 may be sized and dimensioned to accept the infrared or other optical sensors 18 such that two of the distal-most sensors 18 lie in the same plane as the etched line pattern 108. For example, the sensors 18 may be spaced apart by a multiple of 1.5 times the etched pattern spacing. This method of spacing sensors 18 may be useful with direction-detecting rotary encoders, and the sensor processing is described in more detail herein with regard to FIGS. 8A-8C.

The placement of the pair of distal sensors 18 on arm 96 of handle 70 and corresponding indicators 108 on stationary outer tube 62 provides the data input to the sensors 18 corresponding to the rotational movement of the drivers 64, 66. As the handle 70 is rotated to drive one or both of drivers 64, 66, the arm 96 of the handle 70 simultaneously rotates about the central longitudinal axis L. As the pair of distal sensors 18 in the arm 96, pass over the repeating pattern of indicators 108 on the outer tube 62, the sensors 18 are able to determine the change in angular position in real time. Although this embodiment exemplifies a rotating arm and handle assembly passing over a stationary outer tube with etched markings, it will be appreciated that the positioning could be reversed or reconfigured, for example, with the patch and sensors placed on the stationary tube and the markings or indicators on a moveable component.

The third opening 106 may be configured to receive third patch sensor 18 that is able to view indicator 90 on the flange 84 when the clutch collar 68 is in the rear-most position (as shown in FIG. 5B). In particular, the arm 96 of the driver handle 70 has a third sensor-accepting opening 106 that aligns with the clutch collar 68, such that the sensor 18 can detect the presence or absence of the collar 68 due to the etched line 90 that appears circumferentially around the widened lip of the flange 84. When the clutch collar 68 is in the forward-most position (as shown in FIG. 5A), the etched line 90 is not visible to third sensor 18 and the driver handle 70 only turns the inner driver 64. When the clutch collar 68 is in the rear position (as shown in FIG. 5B), the etched line 90 is visible to the third sensor 18 and both the inner and outer drivers 64, 66 rotate at the same rate.

Figure 7:
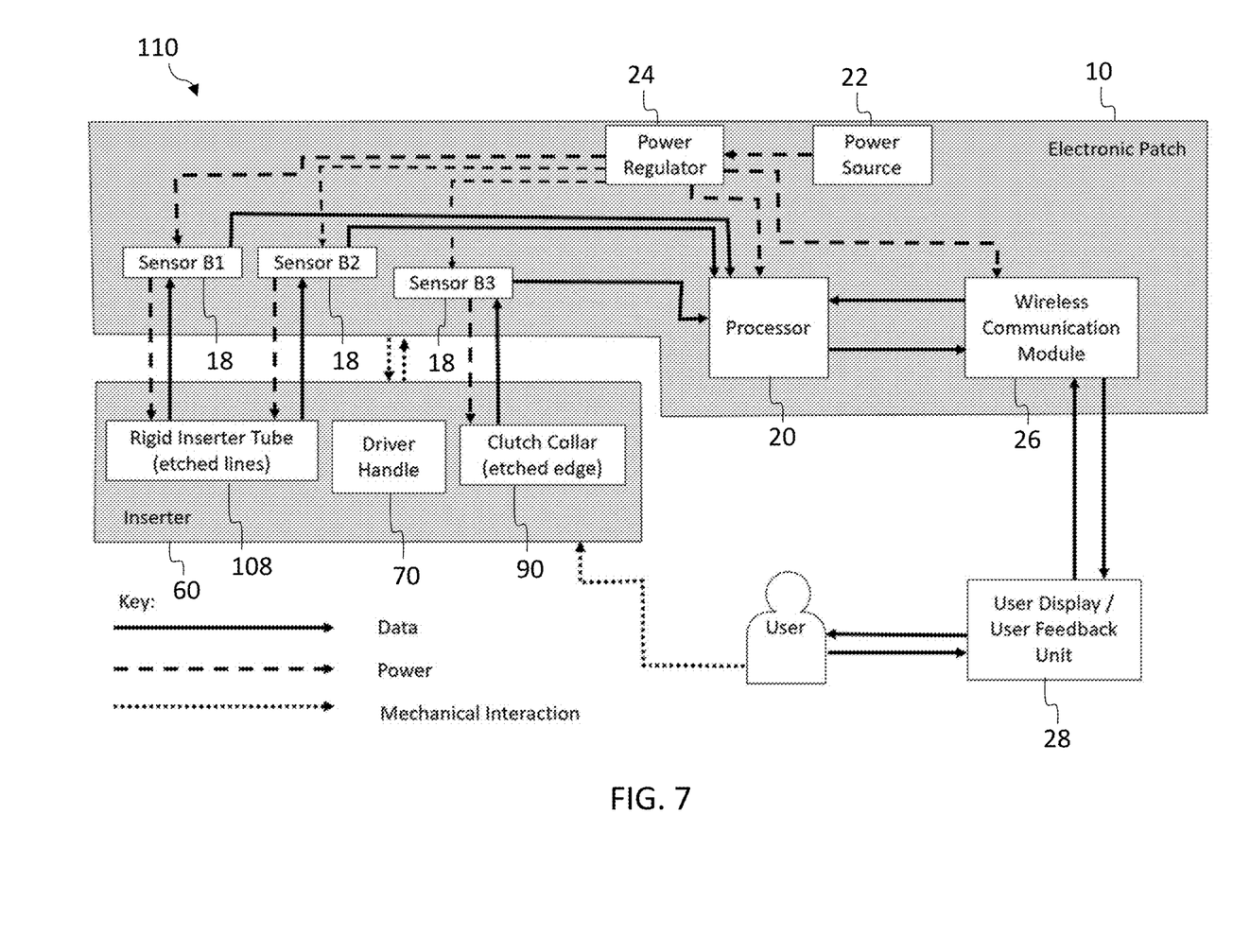
FIG. 7 is an electronics information flow chart for the system components according to one embodiment.

Turning now to FIG. 7, a flowchart 110 shows the system of electronics information flow including the data, power, and mechanical interactions between the system components according to one embodiment. In the embodiment shown, electronic patch 10 includes sensors B1, B2, B3, processor 20, power source 22, power regulator 24, and wireless communication module 26. Inserter 60 includes driver handle 70, radial etched lines 108 on the rigid inserter tube 62, and single etched edge 90 on the clutch collar 68. As the user operates the instrument 60, information about the instrument 60 and the implant 200 is provided to the user on the user display hub or user display/feedback unit 28. Sensors B1, B2 view the etched lines 108 on the outer tube 62 and sensor B3 views the etched line 90 on the clutch collar 68, and relay the information to the on-board processor 20. The processor 20 translates the raw sensor data to implant height and lordotic profile, for example, and sends this information to the user display module 28 via the wireless communication module 26. The power source 22 provides power and the regulator 22 transforms and distributes power to the different electronic components 14.

Alternatively, the division of tasks between the on-board processor 20 and the processor associated with the user display hub 28 may be reconfigured. For example, the wireless control unit 26 on the patch 10 may be configured to only transmit raw sensor data, and the processor on the user display hub 28 may take on the responsibility of processing the data, for example, based on implant selection. This allows the patch 10 to have lower power and processing requirements.

Figure 8A:
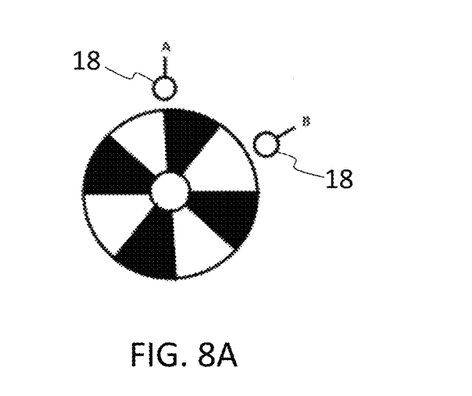
FIGS. 8A-8C show examples of sensor displacement and signal reading, respectively.
Figure 8B:
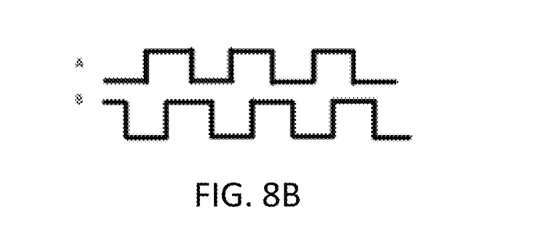
Figure 8C:
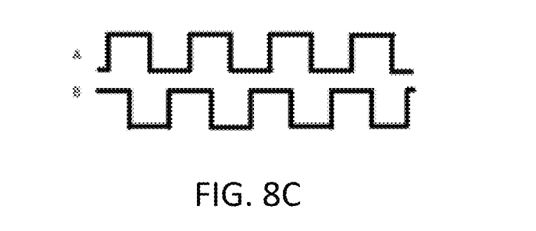

With further emphasis on FIGS. 8A-8C, in the case of infrared optical sensors 18, the sensor information from sensors 18 may be read or decoded using one of the following methods. FIG. 8A shows a simplified diagram of regularly spaced shaded/etched regions and sensor displacement of n*1.5 cycles. FIG. 8B shows signal reading in case of clockwise rotation as sensor A value changes to match that of sensor B. FIG. 8C shows signal reading in case of counterclockwise rotation as sensor A value changes to be opposite of sensor B value.

The patch 10 may use the following framework for direction-detecting rotary encoders. All of the infrared sensors 18 may have an emitter and a receiver that senses the reflected infrared light. As the B1 and B2 sensors pass over the alternating etched lines 108, the signal alternates between high and low, and the changing signal indicates change in angular position. The second sensor 18, which is spaced n*1.5 cycles away, helps to interpret direction of movement based on whether the second sensor's value changes to the same or different value from that of the first sensor 18.

The width of the etched stripes 108 dictates the fidelity of the angular position read-out. The way that this displacement translates to implant height depends on the pitch of the threaded actuator 228 and the relative angles of the ramps 222, 224, 226 within the implant 200. The user will select an implant size and variety on the user display hub 28, and this information may be transmitted to the processor 20 through the wireless communication unit 26 so that accurate implant profile information can be calculated. As the user slides the clutch collar 68 back and forth, sensor B3 will detect the collar position, which will inform implant status in cases where the implant has two independent driven components that are engaged and unengaged with the collar 68.

This calculated implant profile will be fed back to the wireless communication unit 26, which will transmit it to the user display unit 28. The user display unit 28 may be a standalone unit or may take the form of pre-existing robotic and/or navigation platforms. The user display unit 28 may display qualitative feedback such as anterior and posterior heights of the implant or lordotic profile. This information may also be translated into a graphic, such that the user can visualize the implant expanding.

Although the described embodiment exemplifies that the sensors detect implant expansion or lordotic profile, it can be appreciated that with different sensors and placement on various instruments, other parameters may be communicated to a user with a similar patch. For example, instrument information, such as instrument articulation and internal stress experienced by an instrument, may be determined. In one alternative embodiment, the sensors 18 may include strain gauges. Using different sensors 18, such as strain gauges, arranged on different instruments may provide different values to the user. For example, the patch 10 with a strain gauge placed along deformity-manipulation tools may give the user feedback about the stiffness of the deformity. The patch 10 with a strain gauge placed transversely around a driver shaft may give torque read-out information, potentially supplementing or substituting mechanical torque limiters. It will be appreciated that the sensors 18 may be used to obtain different types of information about the patch 10, the instrument 60, the implant 200, or other devices or instruments.

Advantageously, the patches, instruments, and implant systems and associated devices described herein can be used to provide valuable information to the user in real time. For example, the smart sensor patch may be affixed to an inserter instrument, which installs expandable implants. The patch may come pre-sterilized and pre-charged, for example, ready for a single surgical use. In this manner, the end user is not required to sterilize or charge the patch for use. As the implant is expanded in situ, the sensor patch obtains information, such as implant height and lordotic profile, from the inserter instrument and relays this information to the user in real time.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A system for obtaining implant information in real time comprising:
    a smart electronic patch comprising a substrate with a plurality of electronic components electronically connected to one another, wherein the plurality of electronic components include one or more sensors, a processor, a power source, and a wireless transmitter;
    an expandable implant configured to expand in height and/or lordosis; and
    an instrument for installing the expandable implant, wherein the instrument comprises a proximal tube with a plurality of indicators readable by the one or more sensors, a threaded rod extending from the proximal tube and having a distal tip configured to couple to the implant, more coaxial inner and outer drivers positioned through the proximal tube for coupling to the implant and independently adjusting an anterior height and a posterior height of the implant, and a handle for turning one or both of the inner and outer drivers, wherein the plurality of indicators on the proximal tube include regularly spaced alternating etched lines placed in a radial pattern, wherein the handle includes an arm with one or more through openings configured to receive the one or more sensors on the patch, and wherein as the driver rotates, the one or more sensors on the patch detects movement to obtain raw sensor data, the processor on the patch translates the raw sensor data to implant information, and the wireless transmitter on the patch sends the implant information to a user display.

2. The system of claim 1, wherein the one or more sensors include a plurality of infrared optic sensors.

3. The system of claim 1, wherein the smart electronic patch is pre-sterilized and pre-charged.

4. The system of claim 1, wherein the user display is a screen for displaying the implant information to a user.

5. A system for obtaining surgical information in real time comprising:
    an inserter instrument for installing an expandable implant, the inserter instrument extending along a central longitudinal axis and including; an outer tube, a threaded rod extending from the outer tube and having a distal tip configured to attach to the implant, a pair of coaxial drivers positioned through the outer tube for coupling to the implant and independently adjusting an anterior height and a posterior height of the implant, a clutch collar moveable to control rotation of the drivers, and a handle for turning one or both of the drivers, wherein the handle includes an arm with one or more through openings; and
    a smart electronic patch affixed to the handle of the inserter instrument, the smart electronic patch comprising a substrate with a plurality of electronic components electronically connected to one another, wherein the plurality of electronic components include a pair of sensors, a processor, a power source, and a wireless transmitter, the pair of sensors for viewing a plurality of indicators on the outer tube of the instrument, and a third sensor for viewing an indicator on the clutch collar of the instrument, wherein the plurality of indicators on the outer tube include regularly spaced alternating etched lines placed in a radial pattern, wherein the third sensor is configured to detect a position of the clutch collar, and wherein as the handle rotates, the pair of sensors on the patch detects the plurality of indicators on the outer tube.

6. The system of claim 5, wherein the clutch collar includes a proximal hub with a plurality of splines and a distal hub with a plurality of splines separated by a flange.

7. The system of claim 6, wherein the clutch collar is configured to translate along the central longitudinal axis, and the outer tube defines a seat for receiving the distal hub in a forward position and the handle defines a seat for receiving the proximal hub in a rear position.

8. The system of claim 6, wherein the indicator on the clutch collar is an etched line around a perimeter of the flange.

9. The system of claim 5, wherein the pair of sensors include infrared sensors having an emitter and a receiver that senses reflected infrared light to obtain a signal, wherein as the pair of sensors pass over the alternating etched lines, the signal alternates between high and low, thereby indicating a change in angular position.

10. The system of claim 9, wherein the pair of sensors are spaced n*1.5 cycles away from one another to interpret direction of movement of the handle.

* * * * *